US006991651B2

(12) United States Patent
Portney

(10) Patent No.: US 6,991,651 B2
(45) Date of Patent: Jan. 31, 2006

(54) ADJUSTABLE INTRAOCULAR LENS SYSTEM AND INTRAOCULAR LENSES THEREFOR

(76) Inventor: Valdemar Portney, 11940 N. Riviera, Tustin, CA (US) 92782

( * ) Notice: Subject to any disclaimer, the term of this patent is extended or adjusted under 35 U.S.C. 154(b) by 0 days.

(21) Appl. No.: 10/721,155

(22) Filed: Nov. 25, 2003

(65) Prior Publication Data

US 2004/0106993 A1    Jun. 3, 2004

Related U.S. Application Data

(63) Continuation-in-part of application No. 10/306,352, filed on Nov. 27, 2002.

(60) Provisional application No. 60/480,446, filed on Jun. 21, 2003.

(51) Int. Cl.
*A61F 2/16*     (2006.01)
(52) U.S. Cl. .................................................... 623/6.34
(58) Field of Classification Search ...... 623/6.32–6.39, 623/5.13–5.15, 6.11, 6.14–6.21
See application file for complete search history.

(56) References Cited

U.S. PATENT DOCUMENTS

| | | | | |
|---|---|---|---|---|
| 4,434,515 A | * | 3/1984 | Poler | 623/6.41 |
| 4,624,669 A | * | 11/1986 | Grendahl | 623/5.13 |
| 4,810,082 A | * | 3/1989 | Abel, Jr. | 351/160 R |
| 4,842,601 A | * | 6/1989 | Smith | 623/6.34 |
| 5,019,097 A | * | 5/1991 | Knight et al. | 623/5.13 |
| 5,098,444 A | * | 3/1992 | Feaster | 623/6.36 |
| 5,366,502 A | * | 11/1994 | Patel | 623/6.27 |
| 5,814,103 A | * | 9/1998 | Lipshitz et al. | 623/6.34 |
| 5,968,094 A | * | 10/1999 | Werblin et al. | 623/6.34 |
| 6,113,633 A | * | 9/2000 | Portney | 623/6.32 |
| 6,197,058 B1 | * | 3/2001 | Portney | 623/6.34 |
| 6,537,281 B1 | * | 3/2003 | Portney | 606/107 |
| 6,616,691 B1 | | 9/2003 | Tran | |
| 6,827,738 B2 | * | 12/2004 | Willis et al. | 623/6.43 |
| 6,849,091 B1 | * | 2/2005 | Cumming | 623/6.21 |
| 2002/0173846 A1 | * | 11/2002 | Blake et al. | 623/6.18 |
| 2003/0109926 A1 | * | 6/2003 | Portney | 623/6.37 |

* cited by examiner

*Primary Examiner*—Corrine McDermott
*Assistant Examiner*—Cheryl Miller
(74) *Attorney, Agent, or Firm*—Walter A. Hackler

(57) ABSTRACT

An adjustable intraocular lens system is provided by detachably attaching a secondary intraocular lens having a thin, contact lens-type optic onto a primary intraocular lens that has previously been implanted into an individual's eye. The preliminary intraocular lenses have two or more shallow, narrow slits formed adjacent the optical peripheries thereof. These slits may be formed in or through the preliminary intraocular lens optic itself or outside the optic in tabs, in haptic attachment regions or in plate-type haptics. The associated secondary intraocular lens optics are formed having two or more insertion tabs extending radially from the optical peripheries thereof. The secondary intraocular insertion tabs are shaped and located to penetrate corresponding ones of the primary intraocular lens slits and have wedge-shaped free end regions to facilitate slit insertion. The secondary intraocular lens provides a required power correction to the primary intraocular lens to which it is attached.

4 Claims, 6 Drawing Sheets

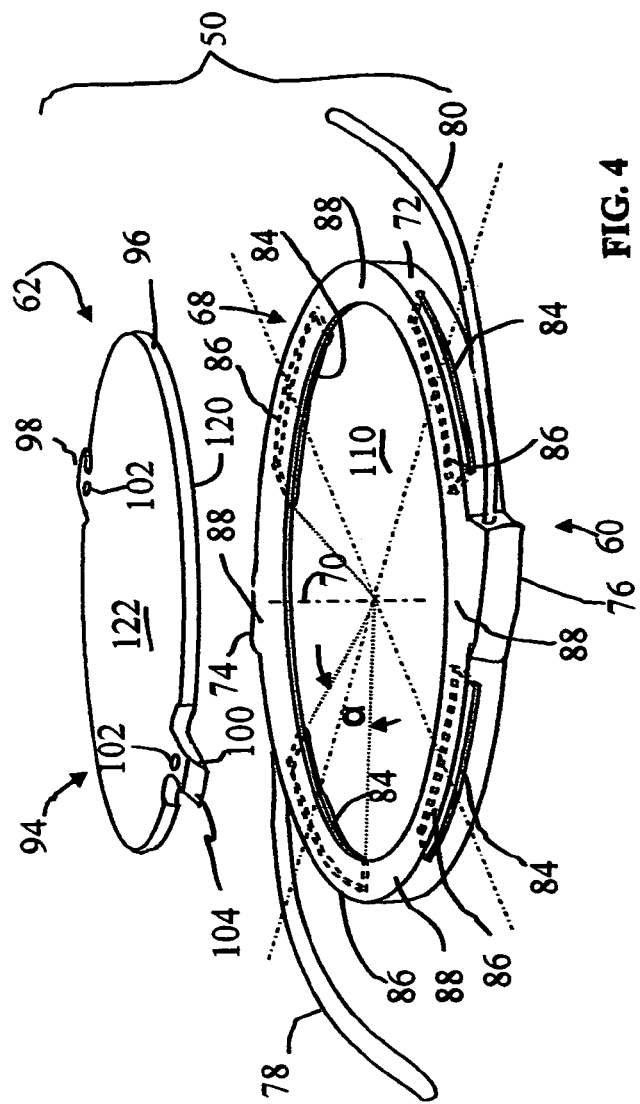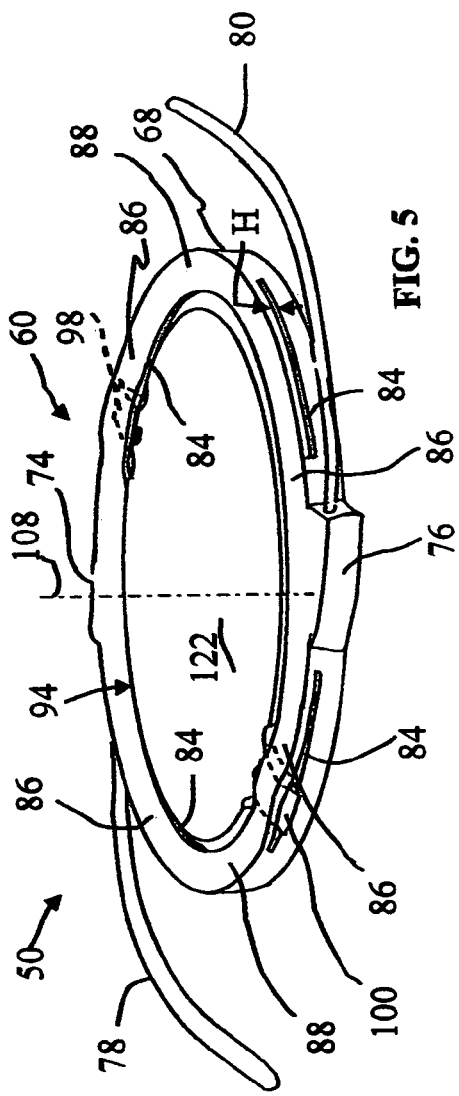

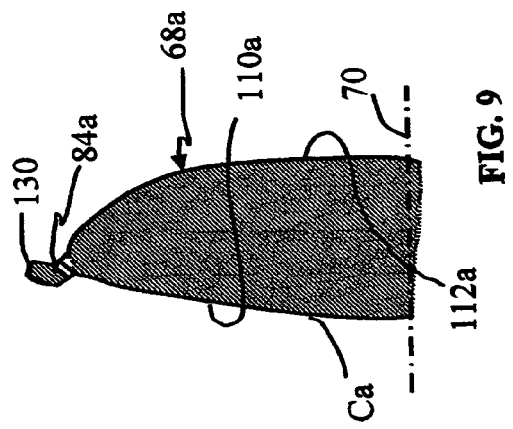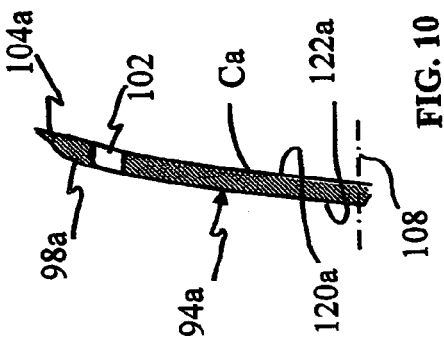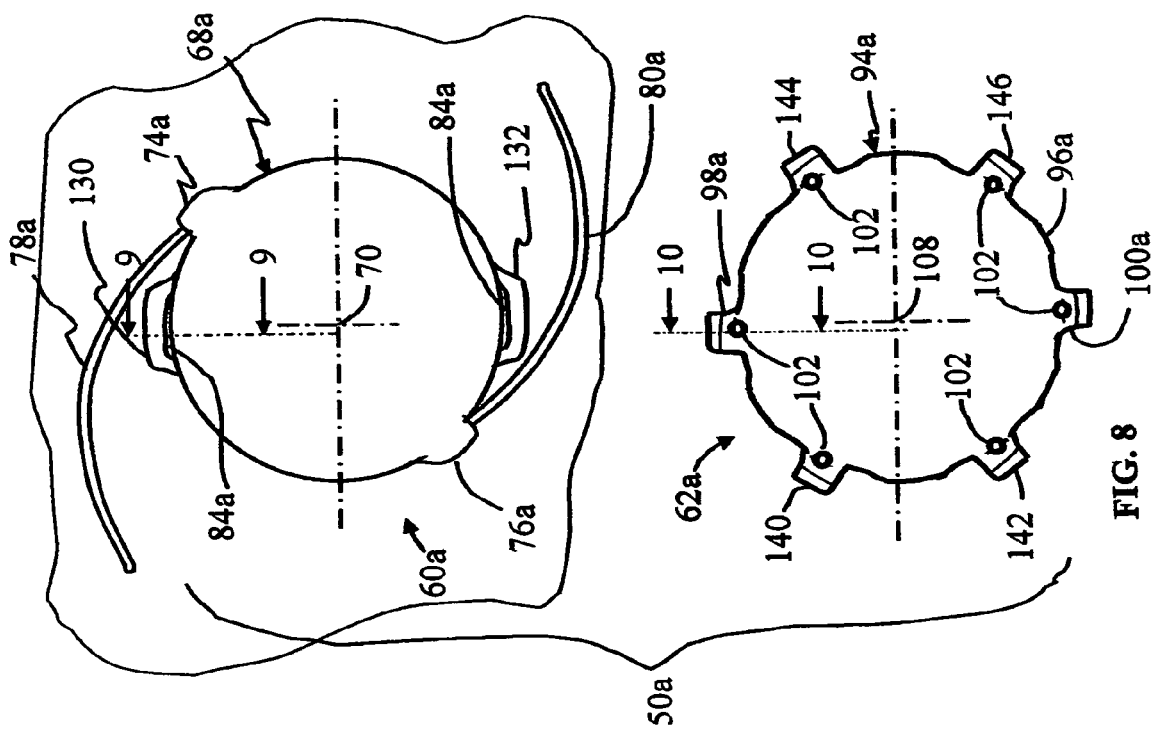

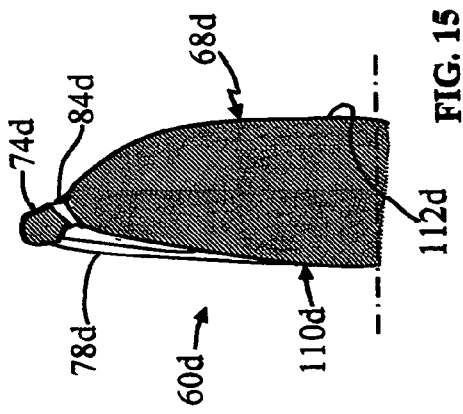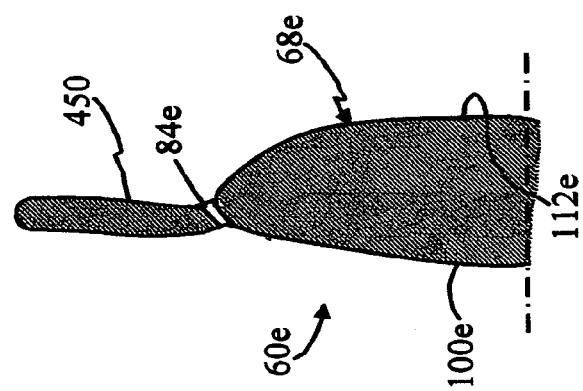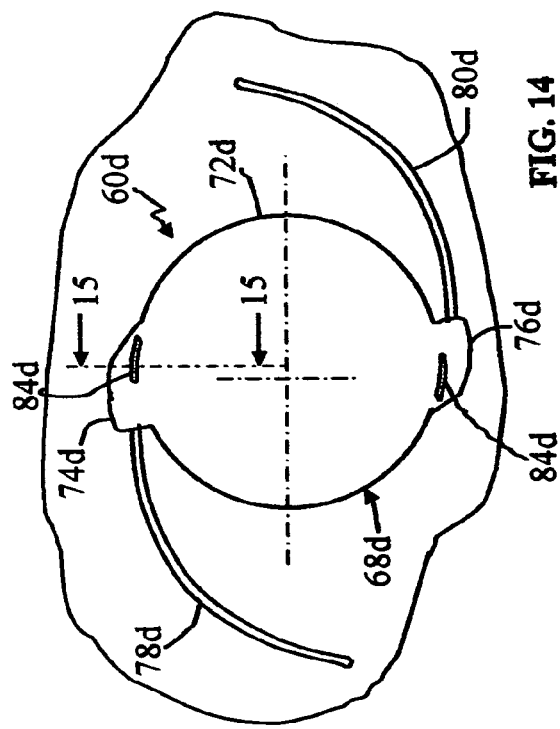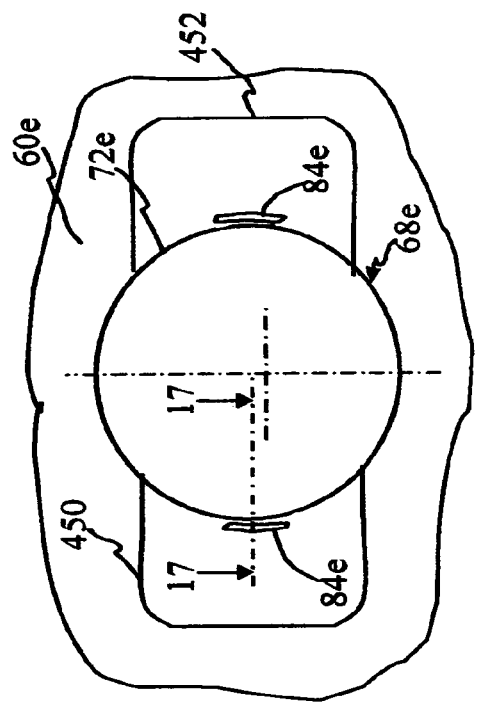

ADJUSTABLE INTRAOCULAR LENS SYSTEM AND INTRAOCULAR LENSES THEREFOR

RELATED PATENT APPLICATION

This application depends on, and is converted from, my prior provisional application Ser. No. 60/480,446, filed on Jun. 21, 2003 and having the same title. Such provisional application is incorporated hereinto in its entirety by specific reference. This application is also a continuation-in-part (CIP) of applicant's application Ser. No. 10/306,352, filed Nov. 27, 2002.

BACKGROUND OF THE INVENTION

1. Field of the Invention

The present invention relates generally to the field of ophthalmics, more particularly to ophthalmic devices, and still more particularly to ophthalmic devices known as intraocular lenses (IOLs).

2. Background Discussion

An individual's natural crystaline optical lens may become defective, for example, as a result of cataracts or trauma. The current corrective practice is to surgically remove the defective natural lens from the individual's eye (rendering the eye a so-called aphakic eye) and implant into the aphakic eye an artificial lens called an intraocular lens (IOL).

Such IOLs may be constructed of a hard, rigid material, most commonly, an optical grade of polymethyl methacrylate (PMMA). IOLs may alternatively be constructed from an elastically deformable material so they can be rolled or folded for insertion into a patient's eye through a much smaller ocular incision than is required for a rigid IOL. Elastically deformable IOLs are commonly constructed from an optically clear, high refractive index, biocompatible silicone or acrylic material.

IOLs may also be implanted in phakic eyes, that is, eyes still having a usable natural optical crystalline lens. In phakic eyes the implanting of a corrective IOL is an often-attractive alternative for some individuals to wearing corrective spectacles or contact lenses, or having surgical procedures, such as laser sculpting of the cornea, performed.

In an aphakic eye, an IOL is now most commonly implanted in the eye's posterior chamber, in the general location from which the defective natural crystaline lens was previously been removed. In contrast, a corrective IOL for a phakic eye is most commonly implanted in the anterior chamber of the eye, but may sometimes be implanted in the posterior chamber or on top of the natural crystaline lens.

Regardless of the reason for implanting an IOL, or the implant location of the IOL, a principal objective of the invention disclosed in my below-cited patents and of the present application is to provide a dual IOL system in which corrections to spherical, cylindrical and/or add power of a primary IOL can be easily made with minimal invasive action to a patient's eye, by the implanting of a secondary IOL.

Corrective intraocular lens systems are disclosed in my U.S. Pat. No. 6,197,058 B1, issued Mar. 6, 2001, and U.S. Pat. No. 6,537,281 B1, issued Mar. 25, 2003, both of which are incorporated herein in their entirety by specific reference. These prior patents of mine disclose a primary intraocular lens having a narrow recess or groove formed into the anterior surface of the optic adjacent peripheral optic edge regions, and which may extend completely or only partially around the optic. These patents further disclose an elastically deformable, corrective secondary intraocular lens which provides spherical, cylinder and/or add power corrections to the primary intraocular lens, as may, for example, be needed subsequent to the implanting of the primary IOL if the primary IOL has, for any reason, been inaccurately selected or implanted.

The secondary IOL disclosed in the above-cited patents has lens attachment tabs sized to be received into the recess or groove formed in the primary IOL, so that the secondary lens can be detachably attached to the primary intraocular lens. The secondary intraocular lens is disclosed as formed from an elastic material such as a silicone or acrylic material.

Although the corrective IOL systems disclosed in my above-cited patents offer many important advantages, the present invention includes improvements to the disclosed corrective intraocular lens system in the area of improving the detachably attachment of the secondary intraocular lens to the primary intraocular lens.

SUMMARY OF THE INVENTION

An adjustable intraocular lens system for an individual's eye comprises a primary intraocular lens having an optic with an optical axis, a peripheral edge, an anterior surface and a posterior surface. The preliminary intraocular lens optic has a primary optical power, the primary intraocular lens having a narrow slit formed adjacent the peripheral edge of the primary intraocular lens optic. Attachment means are fixed to the primary intraocular lens optic for maintaining the optical axis thereof centered along the optical axis of an individual's eye.

Further included is a secondary intraocular lens having an optic, which preferably has a central thickness between about 0.1 mm and about 0.4 mm, with an anterior surface and a posterior surface, the optic having a secondary optical power and having an attachment tab extending generally radially therefrom. The attachment tab is sized to penetrate the primary intraocular lens slit with the secondary intraocular lens optic posterior surface laying against the primary intraocular lens optic anterior surface, whereby the secondary intraocular lens optic power provides optical power correction to the primary intraocular lens optic power.

The primary intraocular lens slit may be formed through the primary intraocular lens optic, or the primary intraocular lens optic may be formed having a tab extending generally radially from the optic edge, the slit being formed in such tab. In a variation, the primary intraocular slit is formed in the attachment means adjacent the primary intraocular lens optic peripheral edge. Or, a plurality of slits may be formed in regions of the primary intraocular lens adjacent the primary intraocular optic peripheral edge The tab radially extending from the secondary intraocular lens optic is preferably wedge-shaped, being tapered in thickness toward a free end of the tab, so as to facilitate insertion of the tab into the primary intraocular lens slit. Moreover, it is preferred that the secondary intraocular lens optic have a plurality of attachment tabs extending radially from the secondary intraocular lens optic in locations enabling penetration of a selected one of the tabs into the primary intraocular lens slit.

An adjustable intraocular lens system for an individual's eye comprises a primary intraocular lens having an optic with an optical axis, a peripheral edge, an anterior surface and a posterior surface, the preliminary intraocular lens optic having a primary optical power. The primary intraocular lens has a plurality of narrow slits formed adjacent the peripheral edge of the optic. Attachment means are fixed to the primary intraocular lens optic for maintaining the primary intraocular lens optic optical axis centered along the optical axis of the individual's eye. The primary intraocular lens may comprise a dual optic intraocular lens, for example, a dual optic accommodating intraocular lens consisting of two spaced-apart lenses.

A secondary intraocular lens has an optic with an anterior surface and a posterior surface, the secondary intraocular lens optic, which may have a central thickness between about 0.1 mm and about 0.4 mm, has a secondary optical power and has a plurality of attachment tabs extending generally radially from the optic. The attachment tabs are sized and located to penetrate the primary intraocular lens slits are wedge-shaped, each tab being tapered in thickness toward a free end of the tab, so as to facilitate insertion of said tab into a corresponding one of said primary intraocular lens slits, with the secondary intraocular lens optic posterior surface laying against the primary intraocular lens optic anterior surface, whereby the secondary intraocular lens optic power provides optical power correction to the primary intraocular lens optic power. In this regard a curvature of the secondary intraocular lens optic posterior surface matches a curvature of the primary intraocular lens optic anterior surface, The primary intraocular lens slits are formed through the primary intraocular lens optic, or the primary intraocular lens optic is formed having a plurality of tabs extending generally radially from the optic edge, the slits being formed in the primary intraocular lens optic tabs. The primary intraocular lens slits may be angled inwardly from the primary intraocular lens optic anterior surface and radially outwardly from the optical edge. Each of the plurality of primary intraocular lens slits preferably have a slit height of between about 0.1 mm and about 0.25 mm.

The plurality of primary intraocular lens slits preferably comprises two peripherally spaced-apart slits, and the plurality of secondary intraocular optic tabs includes at least two tabs located such that the tabs can be individually inserted into the two primary intraocular lens slits, whereby orientation of the secondary intraocular lens relative to the primary intraocular lens can be selected to provide required power adjustment. In this regard, the plurality of secondary intraocular lens tabs may comprise two peripherally spaced-apart tabs and the plurality of primary intraocular slits includes at least two slits located such that the two secondary intraocular lens tabs can be individually inserted into the primary intraocular lens slits, whereby orientation of the secondary intraocular lens relative to the primary intraocular lens can be selected to provide required power adjustment.

It is preferred that each of the plurality of secondary intraocular lens optic tabs has a small hole formed at a base thereof so that an instrument can be inserted into the hole to assist the installation of a tab into a primary intraocular lens slit.

Individually, a secondary intraocular lens comprises an optic with an anterior surface, a posterior surface and a peripheral edge, the optic having a secondary optical power and having an attachment tab, preferably, plurality of attachment tabs, extending generally radially from the optic peripheral edge, the tab or tabs being wedge-shaped, tapering in thickness toward a free end thereof, said optic having a central thickness between about 0.1 m and about 0.4 mm. The secondary optic is formed from an elastically-deformable, biocompatible material, selected from the group consisting of silicone and acrylic materials. Preferably, each attachment tab has a small positioning hole formed in a base region thereof. The secondary optical power includes a spherical dioptric power between about −3 and about +3, a cylinder dioptric power between about −5 and about +5 and an add dioptric power between about 0.0 and about +4.

Individually, a primary intraocular lens comprises an optic with an optical axis, a peripheral edge, an anterior surface and a posterior surface, the preliminary intraocular lens optic having a primary optical power which includes a spherical dioptric power between about −10 and about +35, a cylinder dioptric power between about −10 and about +10 and an add dioptric power between about 0.0 and about +4. The primary intraocular lens may comprise a dual optic intraocular lens. Moreover, the primary intraocular lens may comprise a single or dual optic accommodating intraocular lens, the accommodation may be provided by movement of the lens or by changing the shape of the lens and may be characterized by an accommodating range expressed in dioptric power. In this regard, the accommodating dioptric power range may be between about 0.0 and about +4.

The primary intraocular lens has a slit, or a plurality of slits, formed adjacent the peripheral edge of the primary intraocular lens optic; and includes attachment means fixed to the primary intraocular lens optic for maintaining the primary intraocular lens optic optical axis centered along the optical axis of an individual's eye. The slits may be formed in the primary intraocular lens optic, or in the attachment means adjacent the preliminary intraocular lens optic peripheral edge. Alternatively, the preliminary intraocular lens optic is formed having a tab radially extending from said peripheral edge thereof, a slit being formed in the tab. The slit or slits may be formed at an angle, being slanted inwardly from the primary intraocular lens optic anterior surface and radially outwardly. Each slit preferably has a slit height of between about 0.1 mm and about 0.25 mm and has an arc length between about 5 degrees and about 80 degrees.

A corresponding method is provided for modifying the optical characteristics of a primary intraocular lens previously implanted in a patient's eye, the primary intraocular lens, which may be a dual optic intraocular lens, having a primary optic with a narrow slit formed adjacent a periphery of the primary optic, and having a primary optical power. The method comprises the steps of forming a thin, elastically deformable secondary optic having a diameter substantially equal to a primary optic diameter at the primary optic slit, having a secondary optical power and having an insertion tab extending radially outward from a secondary optic peripheral edge.

The method further includes the steps of making a small, ocular incision in a patient's eye, inserting the secondary optic into the patient's eye through the ocular incision with the secondary optic posterior surface laying on a primary optic anterior surface so as to combine the secondary optical power with the primary optical power, positioning the secondary optic until the secondary optic tab is adjacent a entrance of the primary intraocular lens slit, and inserting the secondary optic tab into the primary intraocular lens slit, Preferably the step of forming the secondary optic includes forming the secondary optic tab to have a wedge shape, tapering in thickness toward a free end.

When the previously implanted primary intraocular lens has a plurality of slits arranged in a first pattern around the peripheral edge of the primary optic and in proximity thereto, the step of forming the secondary optic includes forming the secondary optic to have a plurality of the insertion tabs extending radially outward from the secondary optic peripheral edge in a second pattern that is compatible with the primary intraocular lens first pattern of slits.

The step of positioning the secondary optic may include positioning the secondary optic in a desired orientation relative to the primary optic so as to provide an optimum optical power combination of the primary and secondary optics. The step of positioning the secondary optic until the secondary optic tab is adjacent a entrance of the primary optic slit includes positioning the secondary optic until at least two of the secondary optic tabs are adjacent corresponding primary intraocular lens slits and then inserting the at least two secondary optic tabs into the corresponding primary intraocular lens slits.

There is further included a method for modifying the optical characteristics of an adjustable intraocular lens system which was previously implanted in an individual's eye, the system including a primary intraocular lens to which is detachably attached a secondary intraocular lens so as to provide combined primary and secondary optical powers, the primary intraocular lens having a primary optic with a narrow slit formed adjacent a periphery of the primary optic and the secondary intraocular lens having an insertion tab extending radially outward from a secondary optic peripheral edge and penetrating the primary intraocular lens slit. The modifying method comprising the steps of making a small, ocular incision in the individual's eye, withdrawing the secondary intraocular lens insertion tab from the primary intraocular lens slit, thereby detaching the secondary intraocular lens from the primary intraocular lens, and explanting the detached secondary intraocular lens from the patient's eye through the ocular incision while leaving the primary intraocular lens implanted in the patient's eye.

The modifying method may include the further steps of implanting, through the ocular incision, another secondary intraocular lens in the patient's eye in place of the explanted secondary intraocular lens, and attaching the other secondary intraocular lens to the primary intraocular lens.

BRIEF DESCRIPTION OF THE DRAWINGS

The present invention can be more readily understood by a consideration of the following detailed description when taken in conjunction with the accompanying drawings, in which:

FIG. 4 is a drawing showing the secondary IOL of FIG. 1 in close proximity to the anterior surface of the primary IOL of FIG. 1, but not yet attached thereto;

FIG. 5 is a drawing showing tabs of the secondary intraocular lens of FIG. 1 detachably installed into corresponding peripheral slits formed in the primary intraocular lens of FIG. 1, with the posterior surface of the secondary lens conforming to the anterior surface of the primary lens, to thereby form an adjustable lens system;

FIG. 8 is a drawing of a variation adjustable intraocular lens system of the present invention, showing a variation primary intraocular lens having an optic to which is attached an opposing pair of filament-type fixation elements (haptics), and showing an opposing pair of radially-extending tabs with slit regions at the optic body periphery, and still further showing a variation secondary intraocular lens having an optic to which are formed a number of attachment tabs radially extending from the periphery of the optic;

FIG. 9 is a transverse cross sectional drawing taken along line 9—9 of FIG. 8 showing a representative tab with a slit region at the optic periphery;

FIG. 10 is a transverse cross sectional drawing taken along line 10—10 of FIG. 8 showing a representative one of the attachment tabs of the secondary intraocular lens optic;

FIG. 14 is a drawing of another variation primary intraocular lens having an optic formed with a pair of haptic-receiving regions radially extending from opposite peripheral edges of the optic and showing a narrow slit formed in each of the haptic-receiving regions;

FIG. 15 is a cross sectional drawing taken along line 15—15 of FIG. 14, showing the angulation of a representative one of the attachment member slits;

FIG. 16 is a drawing of a variation, plate-type primary intraocular lens having an opposing pair of wide, flat attachment members (haptics) joined to the optic, and showing a narrow slit formed in each of the attachment members adjacent the periphery of the optic; and FIG. 17 is a cross sectional drawing taken along line 17—17 of FIG. 16, showing the angulation of a representative one of the haptic slits.

In the various FIGS. The same elements and features are given the same reference numbers and variations are given the original reference numbers followed by an "a", "b" and so on, as the case may be.

DESCRIPTION OF THE PREFERRED EMBODIMENT

Figure 1:
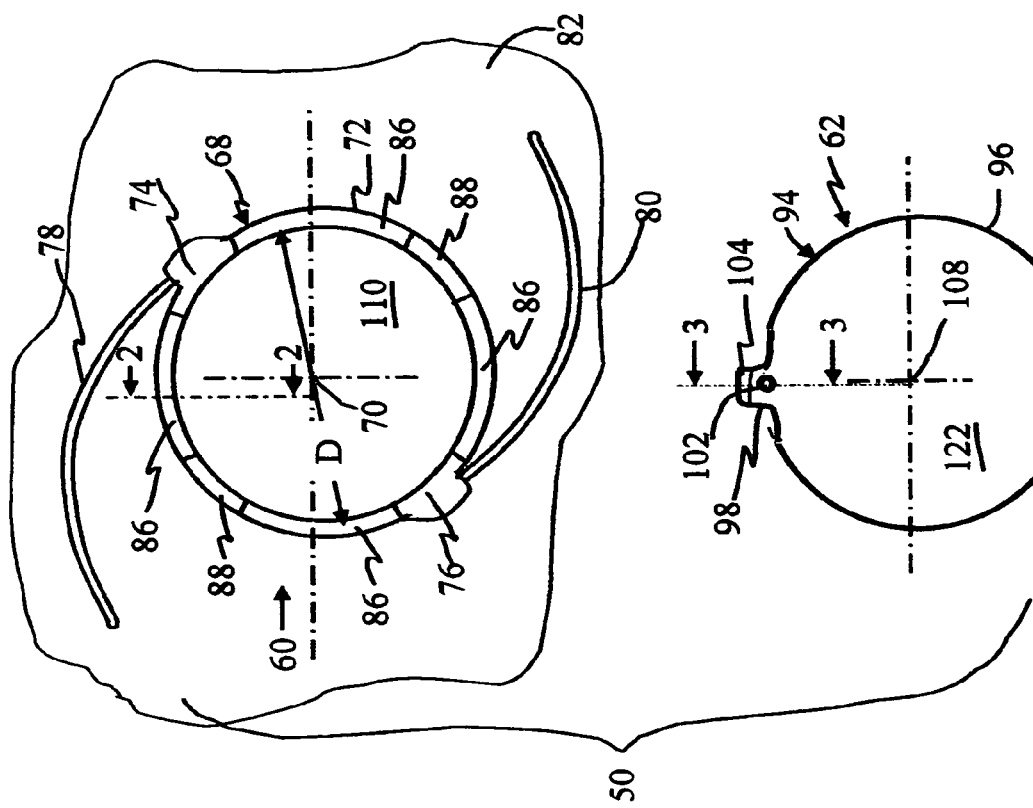
FIG. 1 is an exploded plan view of the adjustable intraocular lens system of the present invention, and includes a drawing of the primary intraocular lens having an optic to which is attached an opposing pair of filament-type fixation elements (haptics), and showing slit regions and connecting regions at the optic periphery and showing a secondary intraocular lens, comprising a secondary optic to which is attached an opposing pair of peripherally located, radially-extending tabs for detachably attaching the secondary intraocular lens to the primary intraocular lens.

Shown in FIG. 1 is an adjustable intraocular lens (IOL) system 50 which comprises a primary IOL 60 and a secondary IOL 62 (both shown separately). Primary IOL 60 comprises an optic 68 having an optical axis 70 and a peripheral edge 72 to opposite regions thereof are formed enlarged regions 74 and 76. Attachment members (called haptics) 78 and 80 are fixed into respective enlarged regions 74 and 76 by means of which primary IOL 60 is fixed in an individual's eye 82 with optic optical axis 70 aligned with the optical axis of the eye (also identified by reference number 70).

Shown formed in primary IOL optic 68, inwardly adjacent peripheral edge 72, are four equally spaced apart slits 84 (FIG. 2), identified in FIG. 1 by overhanging optic regions 86. By means of such radial slits secondary IOL 62 is attached to primary IOL 60, as more particularly described below. Optic regions 88 are located between slits 84 (i.e., overhanging regions 86), the slits defining a useful optic diameter, D. Although it is preferred that all slits 84 be the same size and be spaced equally apart, variations in slit size and spacing are within the scope of the present invention, although such variations are less preferred.

Secondary IOL 62 comprises an optic 94 having a peripheral edge 96 from opposite regions of which attachment or installation tabs 98 and 100 radially extend, the tabs being sized and positioned for easy insertion into an opposite pair of primary IOL optic slits 84. Tabs 98 and 100 have a length sufficient to substantially penetrate primary IOL slits 84. Although it is preferred that tabs 98 and 100 be the same size and be spaced equally apart, variations in tab size and spacing are within the scope of the present invention, although such variations are less preferred.

Figure 3:
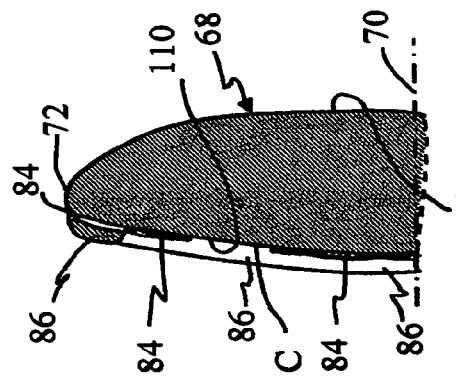
FIG. 3 is a transverse cross sectional drawing taken along line 3—3 of FIG. 1 showing features of a representative tab of the secondary intraocular lens.

Preferably, as shown, each installation tab 98 and 100 is formed having a small hole 102 in a base region thereof, the holes being useful in assisting the positioning of secondary IOL optic 94 for attachment to primary IOL 60. Free or distal end regions 104 and 106 of respective tabs 98 and 100 are wedge shaped, that is, they taper in thickness to a relatively sharp edge as depicted in FIG. 3. Also preferably, regions of secondary optic 94 adjacent tabs 98 and 100 are slightly notched or undercut, as shown in FIG. 1, to increase flexibility of the tabs. Secondary optic 94 is shown having an optical axis 108.

Figure 2:
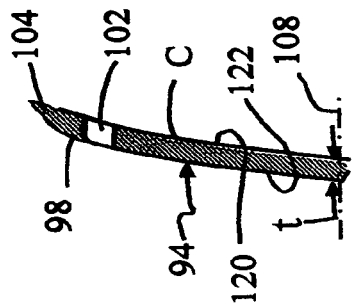
FIG. 2 is a transverse cross sectional drawing taken along line 2—2 of FIG. 1 showing a representative slit region and a representative connecting region at the optic periphery of the primary intraocular lens.

As a consequence of forming slits 84 having overhangs 86, an anterior (i.e., front) surface 110 of primary IOL optic 68 is slightly recessed, as shown in the cross section of FIG. 2. Primary IOL optic anterior surface 110 has a given curvature, C, according to its optical prescription. Primary IOL optic 68 has a posterior (i.e., rear) surface 112. In this regard, there is thus an advantage that curvature, C, of primary IOL optic anterior surface 110 is maintained and the primary IOL optic power varied by changes in the curvature of posterior surface 112.

Primary IOL slits 84 can be fabricated either by molding or a cutting operation depending upon the material used. In a molding operation, a thin plate is incorporated at one of the mold inserts similar to the pin placement for hole fabrication in the optic edge for haptic attachment in a 3-piece intraocular lens. In a cutting operation, a micro drill of appropriate 1 mill diameter is used to cut a slit of about 0.1 mm width. The process is similar to drilling a hole at the lens edge for haptic attachment with addition of rotation of the optic to produce a slit at the optic edge of the required length of about 0.7 mm or longer.

In the cross section of FIG. 3, secondary optic 94 is shown having a posterior surface 120 and an anterior surface 122. It is highly desirable that secondary optic posterior surface 120 have the same, or substantially the same, curvature, C, as primary IOL optic anterior surface 110 so that when secondary optic 94 is attached to primary IOL optic 68, the secondary optic will conform to, and lay closely against, the primary IOL optic. Further, secondary IOL optic 94 has a central thickness, t, that is preferably between about 0.1 mm and about 0.4 mm.

Primary IOL optic 68 preferably has a spherical dioptric power between about −10 and about +35, a cylindrical dioptric power between about −10 and about +10.0, and/or an add dioptric power between about 0.0 and about +4.0. Further, primary IOL 60 may be a posterior chamber IOL or optic 68 thereof may be configured for implanting in the anterior chamber of an eye. Still further, primary IOL 60 lens can be any type of posterior chamber lens, such as single piece or three-piece construction, plate lens, accommodative lens with single or front lens of the double optic accommodative lens system.

Secondary IOL 62 is preferably constructed of an elastically deformable, biocompatible material, such as a silicone or acrylic material, so that the secondary IOL can be implanted through a small ocular incision (not shown) in eye 82. Alternatively, only tabs 98 and 100 may be constructed of elastically deformable material so as to facilitate insertion of the tabs into primary IOL slits 84. It is preferred that secondary IOL optic 94 have a spherical dioptric power between about −3.0 and about +3.0, a cylinder dioptric power between about −5.0 and about +5.0, and/or an add dioptric power between about 0.0 and about +4.0.

FIGS. 4 and 5 illustrate the manner in which secondary IOL 62 of FIG. 1 is detachably attached to primary IOL 60 of FIG. 1. FIG. 4 depicts secondary IOL 62 positioned above adjacent IOL 60 preliminary to attachment of secondary IOL optic 94 to primary IOL optic 68; whereas, FIG. 5 depicts adjustable IOL system 50 after secondary IOL optic 94 has been detachably attached to primary IOL optic 68.

As can be seen in FIGS. 4 and 5, because secondary IOL optic 94 is formed having an opposite pair of installation tabs 98 and 100 and primary IOL optic 68 is formed having two opposite pairs of slits 84 (that is, slits 84 are arranged at 90 degree intervals), the secondary IOL optic can be attached to primary IOL optic in any of four angular orientations, according to required power correction of primary IOL optic. It is also shown in FIG. 4 that slits 84 have an angular width, $\alpha$, (shown for one representative slit) that is preferably between about 5 degrees and about 80 degrees and have a slit height, H, that is between about 0.1 mm and about 0.25 mm. Regions 88 between slits 84 may a width in angular terms of between about 10 degrees and about 160 degrees.

In FIG. 5, secondary optic tabs 98 and 100 are shown extending completely through corresponding ones of primary IOL optic slits 84, thereby assuring secure attachment of secondary IOL optic 94 to primary IOL optic 68.

Figure 6:
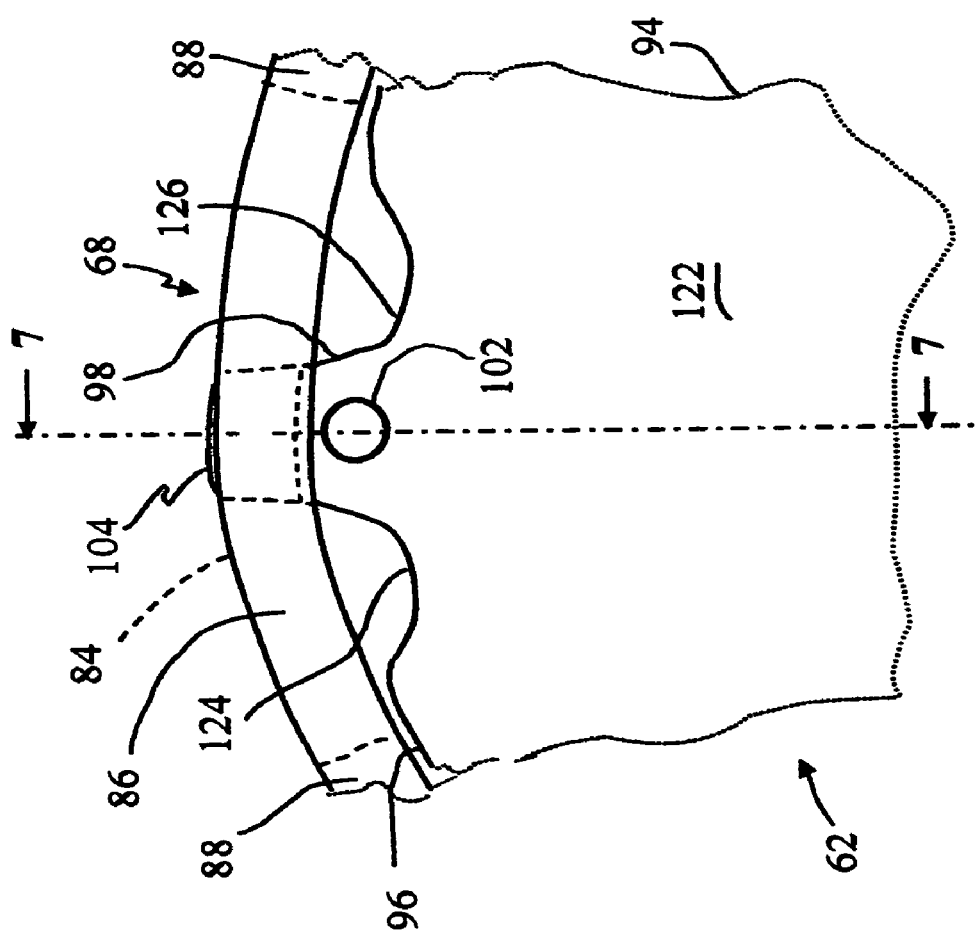
FIG. 6 is a greatly enlarged and detailed drawing showing a representative one of the primary intraocular lens slit regions depicted in FIG. 5, in which a representative tab of the secondary IOL of FIG. 1 is shown inserted.

Shown in FIG. 6, is a very much enlarged drawing showing representative tab 98 of secondary IOL optic 94 inserted into, and penetrating, a representative one of primary IOL slits 84. FIG. 6 also shows arcuate recesses 124 and 126 that are formed on secondary IOL optic edge 96 to opposite sides of tab 98, thereby increasing flexibility of the tab for slit insertion purposes.

Figure 7:
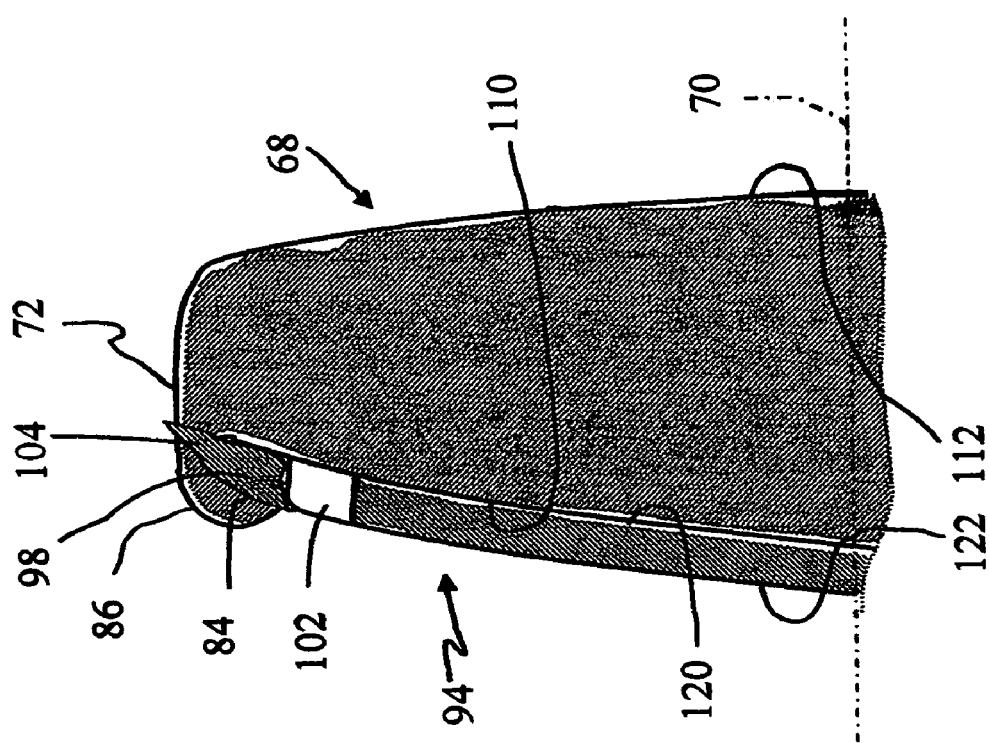
FIG. 7 is a transverse cross sectional drawing taken along line 7—7 of FIG. 6 of the adjustable intraocular lens system of the present invention, showing the primary IOL of FIG. 1 having an optic with a representative slit, and showing the installation of a representative tab of the thin, contact lens-like secondary intraocular lens of FIG. 1 into the corresponding slit formed in the primary intraocular lens for the detachable attachment of the secondary intraocular lens to the primary intraocular to provide a predetermined optical correction thereto.

FIG. 7 is a vertical cross section of the tab-slit insertion region of FIG. 6, showing penetration of tab 98 through slit 84 and showing wedge-shaped end region 104 of tab 98 which facilitates insertion of the tab into the slit. Further shown in FIG. 7 is secondary IOL optic posterior surface 120 laying closely against primary IOL optic anterior surface 110, as previously described.

A variation adjustable intraocular lens system 50*a* is shown in FIG. 8 as comprising a first variation primary IOL 60*a* and a first variation secondary IOL 62*a*. Except as otherwise described first variation primary IOL 62*a* and first variation secondary IOL 62*a* are similar to corresponding primary IOL 60 and secondary IOL 62 described above. Consequently, adjustable IOL system 50*a* is similar to above-described adjustable IOL system 50.

As depicted, primary IOL 60*a* comprises a primary optic 68*a* with a peripheral edge 72*a* having enlarged haptic attachment regions 74*a* and 76*a* to which haptics 78*a* and 80*a*, respectively, are attached. Shown radially extending from opposite edge regions of primary optic 68*a* are short tabs or projections 130 and 132, in each of which a narrow, through slit 84*a* is formed generally parallel to, and adjacent, primary optic edge 72*a* to enable detachable attachment of secondary IOL 62*a* to primary IOL 60*a*.

Secondary IOL 62*a* comprises a secondary optic 94*a* having a peripheral edge 96*a*. Extending radially outwardly from secondary optic edge 96*a* are shown six equally spaced apart, similar attachment tabs 98*a*, 100*a*, 140, 142, 144 and 146, all of which are sized for easy insertion into primary IOL slits 84*a*. A positioning hole 102 is formed in each of secondary optic tabs 98*a*, 100*a*, 140, 142, 144 and 146 adjacent base regions thereof.

As a result of forming secondary IOL optic 94*a* having six equally spaced apart insertion tabs 98*a*, 199*a*, 142, 144, 146 and 148, secondary IOL 62*a* can be attached to primary IOL 60*a* in a number of different angular orientations as may be required to achieve the correct power combination of the two IOLs.

FIG. 9 is a vertical cross sectional drawing of primary IOL optic 68*a* showing angulation, inwardly and radially outwardly, of slit 84*a* in representative tab 130. Also indicated is curvature, Ca, of optic anterior surface.

FIG. 10 is a vertical cross sectional drawing of secondary IOL optic 94*a* showing curvature, Ca, of optic posterior surface 120*a*, and further showing the wedge shapr of distal end region 102*a* of representative insertion tab 98*a*.

Figure 13:
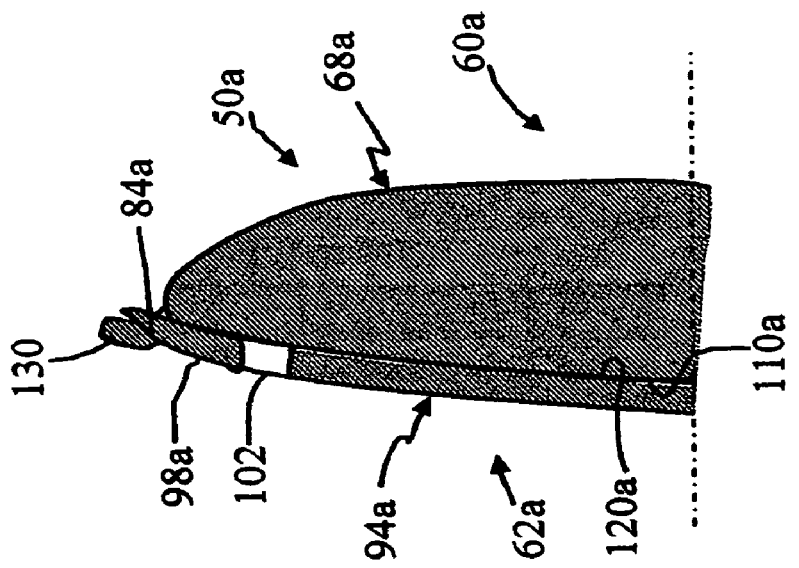
FIG. 13 is third variation cross section (similar to the cross section of FIG. 12) of an adjustable intraocular lens system of the present invention, showing the design of the primary IOL depicted in FIGS. 8 and 9, having an optic and a slit formed into an anterior surface of the optic at the optic edge and showing a corresponding tab of a thin, contact lens-like secondary intraocular lens installed in the primary intraocular lens slit for detachable attachment of the secondary intraocular lens to the primary intraocular lens to provide a predetermined optical correction thereto.
Figure 12:
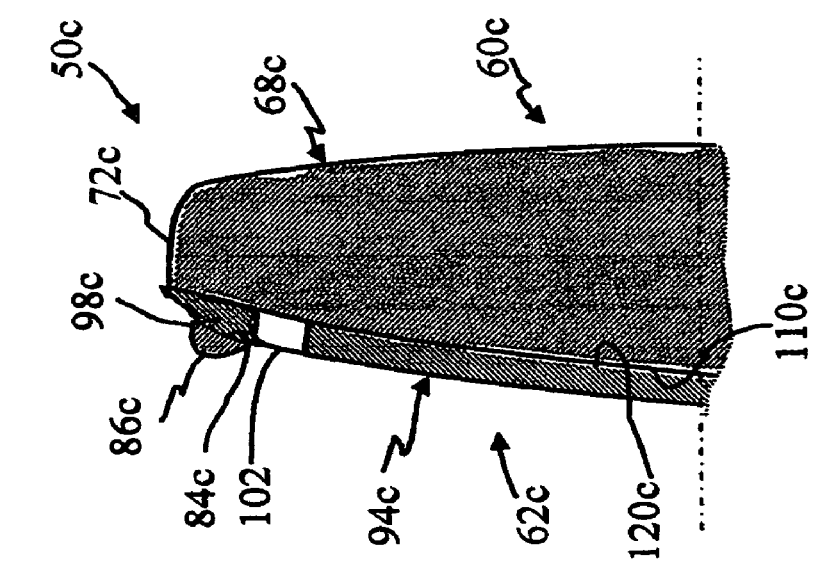
FIG. 12 is a second variation cross section (similar to the cross section of FIG. 11) of another adjustable intraocular lens system of the present invention, showing another alternative design of the primary intraocular lens having an optic and a slit formed into an anterior surface of the optic that does not reach the optic edge, and showing a corresponding tab of a thin, contact lens-like secondary intraocular lens installed in the primary intraocular lens slit region for detachable attachment of the secondary intraocular lens to the primary intraocular lens to provide a predetermined optical correction thereto.
Figure 11:
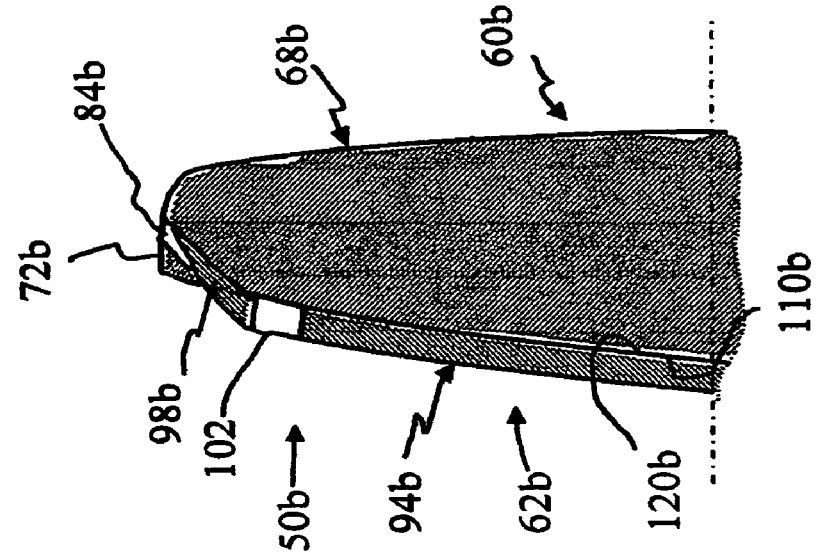
FIG. 11 is variation cross section (similar to the cross sections of FIGS. 7 and 9) of an adjustable intraocular lens system of the present invention, showing a alternative design of the primary intraocular lens having an optic and a slit formed into an anterior surface of the optic adjacent to the optic edge, and showing a corresponding tab of a thin, contact lens-like secondary intraocular lens installed in the primary intraocular lens slit for detachable attachment of the secondary intraocular lens to the primary intraocular lens to provide a predetermined optical correction thereto.

FIGS. 11, 12 and 13 are vertical cross sectional drawings showing three different versions of secondary IOL-to-primary IOL attachments, according to different shapes and locations of primary IOL insertion slits.

FIG. 11 depicts a representative insertion slit 84*b* that is formed through a peripheral edge 72*b* of a primary IOL optic 68*b*, and into which is inserted a representative tab 98*b* of a secondary IOL optic 94*b*. Primary IOL optic 68*b* and secondary optic 94*b* may otherwise be as described above for primary IOL optic 68 and secondary IOL 94 relative to FIG. 1.

FIG. 12, which corresponds directly with FIG. 7, depicts a representative insertion slit 84*c* that is formed adjacent a peripheral edge 72*c* of a primary IOL optic 68*c*, and into which is inserted a representative tab 98*c* of a secondary IOL optic 94*c*. Primary IOL optic 68*c* and secondary optic 94*c* may otherwise be as described above for primary IOL optic 68 and secondary IOL 94 relative to FIG. 1.

FIG. 13 represents the attachment of secondary IOL optic 94*a* to primary IOL optic 68*a* of FIGS. 8–10, showing representative installation tab 98*a* installed in primary IOL optic slit 84*a* that is formed in representative tab 130.

Shown in FIG. 14 is another variation primary IOL 60*d* showing a primary IOL optic 68*d* having an opposing pair of enlarged regions 74*d* and 76*d* into which are received attachment haptics 78*d* and 80*d*, respectively. In that respect primary IOL 60*d* closely resembles primary IOL 60 described above relative to FIG. 1. However, an installation slit 84*d* (for receiving a secondary IOL optic installation tab, such as tab 98, FIG. 1) is formed in each of enlarged, haptic receiving regions 74*d* and 76*d* adjacent, and generally parallel to, primary IOL optic peripheral edge 72*d*, instead of in the optic itself.

FIG. 15 is a vertical cross section of primary IOL 60*d* showing that representative installation slit 84*d* is angled inwardly and radially outwardly through enlarged region 74*d*.

Still another variation primary IOL 60*e* is depicted in FIG. 16. Primary IOL 60*e* is of the plate-type form, having an opposing pair of broad, flat attachment haptics 450 and 452 extending radially from primary IOL optic peripheral edge 72*e*. A secondary IOL optic tab-receiving slit 84*e* is formed in each haptic 450 and 452 adjacent, and generally parallel to, primary IOL optic peripheral edge 72*e*.

FIG. 17 is a horizontal cross section of primary IOL 60*e* showing that representative installation slit 84*e* is angled inwardly and radially outwardly through representative haptic 450.

Thus, described above are several primary IOL variations 60–60*e* and secondary IOL variations 62–62*c*, which paired together in the manner described form several variation adjustable IOL systems 50–50*c*. Individual primary and secondary IOLs been described. A corresponding method for providing an adjustable intraocular system is evident from the foregoing description of the systems.

Although there is described and illustrated herein an adjustable intraocular lens system and intraocular lenses used therewith, and variations thereof, for purposes of illustrating the manner in which the present invention may be used to advantage, it is to be understood that the invention is not limited thereto. Consequently, any and all variations and equivalent arrangements which may occur to those skilled in the applicable art are to be considered to be within the scope and spirit of the invention as set forth in the claims which are appended hereto as part of this application.

What is claimed is:

1. An adjustable intraocular lens system for an individual's eye, said intraocular lens system comprising:
   a. a primary intraocular lens having an optic with an optical axis, a peripheral edge, an anterior surface and a posterior surface, said primary intraocular lens optic having a primary optical power, said primary intraocular lens having a slit formed in and through the primary intraocular lens optic, the slit extending into the anterior surface and out of the peripheral edge of said optic, said optic including an optic region overhanging the slit and anterior surface, said optic further having attachment means fixed to said optic for maintaining said optical axis centered along the optical axis of an individual's eye; and b. a secondary intraocular lens having an optic with an anterior surface and a posterior surface, said optic having a secondary optical power and having a narrow attachment tab extending generally radially outwardly from a peripheral edge of the secondary intraocular lens optic, said attachment tab being sized to penetrate generally radially the primary intraocular lens optic slit with the tab lying under the overhanging optic region and the secondary intraocular lens optic posterior surface laying against the primary intraocular lens optic anterior surface, whereby said secondary intraocular lens optic power provides optical power correction to the primary intraocular lens optic power.

2. The adjustable intraocular lens system as claimed in claim 1, wherein said primary intraocular lens includes a plurality of slits with corresponding overhanging optic regions and said secondary intraocular lens optic has a plurality of attachment tabs extending radially from said secondary intraocular lens optic in locations enabling penetration of a selected one of said tabs into a corresponding intraocular lens slit and under a corresponding overhanging optic region.

3. The adjustable intraocular lens system as claimed in claim 1, wherein said tab radially extending from said secondary intraocular lens optic is wedge-shaped, being tapered in thickness toward a free end of the tab, so as to facilitate insertion of said tab into said primary intraocular lens slit.

4. The adjustable intraocular lens system as claimed in claim 1, wherein said secondary intraocular lens optic has a central thickness between about 0.1 mm and about 0.4 mm.

* * * * *